(12) United States Patent
Mastri et al.

(10) Patent No.: US 9,526,886 B2
(45) Date of Patent: Dec. 27, 2016

(54) COUPLING FOR CONNECTING A TUBE SET TO A TROCAR

(71) Applicant: SurgiQuest, Inc., Milford, CT (US)

(72) Inventors: Dominick Mastri, Bridgeport, CT (US); Kenneth Blier, Cheshire, CT (US)

(73) Assignee: Surgiquest, Inc., Milford, CT (US)

( * ) Notice: Subject to any disclaimer, the term of this patent is extended or adjusted under 35 U.S.C. 154(b) by 156 days.

(21) Appl. No.: 14/133,121

(22) Filed: Dec. 18, 2013

(65) Prior Publication Data

US 2014/0171855 A1   Jun. 19, 2014

Related U.S. Application Data

(60) Provisional application No. 61/739,391, filed on Dec. 19, 2012.

(51) Int. Cl.
*A61M 37/00* (2006.01)
*A61M 39/10* (2006.01)
(Continued)

(52) U.S. Cl.
CPC ............ *A61M 39/105* (2013.01); *A61B 17/34* (2013.01); *A61M 13/003* (2013.01);
(Continued)

(58) Field of Classification Search
CPC .. A61M 39/08; A61M 39/10; A61M 39/1011; A61M 39/105; A61M 2039/082; A61M 2039/1016; A61M 2039/1077; A61M 2039/1083; A61M 2039/1088; A61M 2025/0039; A61M 13/003; A61M 25/0041; A61M 39/06; A61M 2039/1033; A61M 17/34; F16L 37/56;F16L 37/565; A61B 17/34; A61B 17/3401; A61B 17/3415; A61B 17/3417; A61B 17/3421; A61B 17/3462; A61B 2017/3445; A61B 2017/3447; A61B 2017/3449
(Continued)

(56) References Cited

U.S. PATENT DOCUMENTS 2,568,566 A  *  9/1951  Sokolik .......................... 604/26
3,548,607 A  *  12/1970  Pillsbury, Jr. ......... F16L 59/141
                                                                138/114
(Continued)

FOREIGN PATENT DOCUMENTS

WO  WO-9602297 A1  2/1996
WO  WO-2010106091 A1  9/2010

OTHER PUBLICATIONS

Extended Search Report issued Jul. 26, 2016 in connection with co-pending Application EP13864032.1.

*Primary Examiner* — Jason Flick
(74) *Attorney, Agent, or Firm* — Locke Lord LLP; Scott D. Wofsy; Arpita G. Buesing

(57) ABSTRACT

A coupling system is provided for connecting a tube set to a trocar that includes a multi-lumen trocar having a housing that includes a connector, wherein the connector has a plurality of coaxial flow passages defined therein by a plurality of concentric annular walls, a multi-lumen tube set including a plurality of tubes arranged in a parallel relationship, and a coupling including a generally cylindrical body having a first end portion configured to selectively mate with the coaxial flow passages of the connector of the trocar and a second end portion configured for attachment to the parallel tubes of the tube set.

16 Claims, 10 Drawing Sheets

(51) Int. Cl.
*A61M 13/00* (2006.01)
*A61B 17/34* (2006.01)
*A61M 39/08* (2006.01)

(52) U.S. Cl.
CPC ... *A61M 39/1011* (2013.01); *A61M 2039/082* (2013.01); *A61M 2039/1033* (2013.01)

(58) Field of Classification Search
USPC ............ 604/23, 26, 43, 264, 523, 533, 534, 535,604/538
See application file for complete search history.

(56) References Cited

U.S. PATENT DOCUMENTS

| | | | | |
|---|---|---|---|---|
| 5,718,678 | A | * | 2/1998 | Fleming, III ................... 604/43 |
| 7,854,724 | B2 | | 12/2010 | Stearns et al. |
| 7,976,598 | B2 | | 7/2011 | Matula et al. |
| 2003/0014035 | A1 | * | 1/2003 | Trombley et al. ............ 604/500 |
| 2007/0088275 | A1 | * | 4/2007 | Stearns .............. A61B 17/3421 604/164.01 |
| 2008/0082052 | A1 | * | 4/2008 | Schnell et al. ........... 604/165.03 |
| 2010/0185139 | A1 | * | 7/2010 | Stearns .............. A61B 17/3474 604/26 |
| 2012/0150101 | A1 | | 6/2012 | Stearns et al. |
| 2012/0191037 | A1 | * | 7/2012 | Patel .................... F16K 5/0407 604/30 |
| 2012/0245511 | A1 | | 9/2012 | Stearns et al. |
| 2013/0012782 | A1 | | 1/2013 | Stearns et al. |
| 2013/0231606 | A1 | | 9/2013 | Stearns et al. |
| 2014/0074015 | A1 | * | 3/2014 | Mastri ................ A61B 17/3474 604/26 |

\* cited by examiner

COUPLING FOR CONNECTING A TUBE SET TO A TROCAR

CROSS-REFERENCE TO RELATED APPLICATION

The subject invention claims the benefit of priority from U.S. Provisional Patent Application Ser. No. 61/739,391 filed Dec. 19, 2012, the disclosure of which is herein incorporated by reference in its entirety.

BACKGROUND OF THE INVENTION

1. Field of the Invention

The subject invention is directed to laparoscopic surgery, and more particularly, to a coupling for detachably connecting a multi-lumen tube set to a surgical access device used during laparoscopic surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Further, in laparoscopic surgery, electrocautery and other techniques (e.g. harmonic scalpels) create smoke and other debris in the surgical cavity, reducing visibility by fogging the view from, and coating surfaces of endoscopes and the like. A variety of surgical insufflation systems and smoke evacuation systems are known in the art.

SurgiQuest, Inc., Milford, Conn. has developed surgical access devices or trocars that permit access to an insufflated surgical cavity without conventional mechanical seals, and has developed related systems for providing sufficient pressure and flow rates to such access devices, as described in whole or in part in U.S. Pat. No. 7,854,724, the disclosure of which is herein incorporated by reference in its entirety.

SurgiQuest has also developed multimodal systems, and related devices and methods, capable of performing multiple surgical gas delivery functions, including insufflation to standard or specialized surgical access devices or other instruments, such as veress needles and the like, smoke evacuation through standard or specialized surgical access devices, and specialized functions, such as recirculation and filtration of insufflation fluids. Examples of such multimodal systems and related devices are disclosed in U.S. Patent Application Publication 2012/0150101, which is herein incorporated by reference in its entirety.

Multimodal systems typically require the use of a disposable filter cartridge having multiple flow passages, as disclosed in U.S. Pat. No. 7,976,598 and U.S. Patent Application Publication No. 2013/0231606, which are herein incorporated by reference in their entireties. These disposable filter cartridges are installed in an insufflator and are connected to a multi-lumen tube set which communicates with a surgical access device or trocar, such as, for example, the devices disclosed in U.S. Patent Application Publication 2012/0245511, which is incorporated herein by reference in its entirety.

The mechanical connection between the tube set and the surgical access device or trocar is typically a threaded connection and often requires precise alignment of a plurality of flow paths. Achieving this connection can take an inordinate amount of time and can require some level of dexterity. It would be beneficial therefore to provide a coupling system for detachably connecting a multi-lumen tube set to a surgical access device that overcomes these deficiencies.

SUMMARY OF THE INVENTION

The subject invention is directed to a new and useful coupling system for connecting a tube set to a surgical device. The system includes a surgical device having a housing that includes a connector, and a tube set including a coupling having a body adapted and configured to selectively connect with the connector of the surgical device through rotational engagement of the coupling with respect to the connector.

Preferably, the coupling includes a ratcheting clutch mechanism adapted and configured to ensure that a predetermined amount of torque is applied during the rotational engagement of the coupling with the connector. The coupling includes an annular gripping collar formed separate from and mounted to rotate relative to the body of the coupling. A first portion of the ratcheting clutch mechanism is associated with an inner peripheral surface of the annular collar and a second portion of the ratcheting clutch mechanism is associated an outer peripheral surface of the body of the coupling.

In an embodiment of the invention, the surgical device is a multi-lumen trocar that includes a cannula portion extending from the housing and including coaxial inner and outer lumens. In another embodiment, the surgical device is a secondary tube set that includes a single lumen having the housing at one end a leur fitting at an opposite end for connecting with a single lumen trocar.

The subject invention is also directed to a new and useful coupling system for a multi-lumen trocar having a housing that includes a connector. The connector has a plurality of coaxial flow passages defined therein by a plurality of concentric annular walls. The system further includes a multi-lumen tube set having a plurality of tubes arranged in a parallel relationship. The system also includes a coupling including a generally cylindrical body having a first end portion adapted and configured to selectively mate with the coaxial flow passages of the connector of the trocar and a second end portion adapted and configured for attachment to the parallel tubes of the tube set.

Preferably, the second end portion of the body of the coupling includes a plurality of parallel tube fittings for mating with the tubes of the tube set, and the first end portion of the body of the coupling includes an inner flow passage, a medial flow passage surrounding the inner flow passage and an outer flow passage surrounding the medial flow passage.

The second end portion of the body of the coupling includes a first tube fitting communicating with the inner flow passage in the first end portion of the body, a second tube fitting communicating with the medial flow passage in the first end portion of the body and a third tube fitting communicating with the outer flow passage in the first end portion of the body.

The first end portion of the body of the coupling includes an annular engagement channel defined between an interior wall of the body of the coupling and the outer flow passage in the first end portion of the coupling, the annular engagement channel including radially inwardly projecting cam surfaces for interacting with radially outwardly projecting cam followers on an outer annular wall of the connector of the trocar, when the coupling is rotational engaged with the connector of the trocar.

Preferably, an outer peripheral portion of the body of the coupling includes an annular gripping section to facilitate rotation engagement of the coupling with the connector of the trocar. In one embodiment, the annular gripping section is formed integral with the body of the coupling.

In another embodiment, the annular gripping section includes an annular collar formed separate from and mounted to rotate relative to the body of the coupling. Preferably, the annular gripping section includes at least part of a ratcheting clutch mechanism configured to ensure that a predetermined amount of torque is applied during the rotational engagement of the coupling with the connector of the trocar.

A first portion of the ratcheting clutch mechanism is associated with an inner peripheral surface of the annular collar and a second portion of the ratcheting clutch mechanism is associated an outer peripheral surface of the body of the coupling. The coupling is associated with one end of the tube set and a disposable filter cartridge is associated with an opposite end of the tube set.

The subject invention is also directed to a coupling system that can be used in multi-flow applications outside of the medical device field, including, for example, in the chemical processing, agricultural, automotive or aerospace industries. In such a case, the coupling system includes a connector having a plurality of coaxial flow passages defined therein by a plurality of concentric annular walls, and a coupling including a generally cylindrical body having a first end portion that includes a plurality of concentric annular walls that are dimensioned for intimate engagement with the coaxial flow passages of the connector.

The first end portion of the body of the coupling includes an inner flow passage, a medial flow passage surrounding the inner flow passage and an outer flow passage surrounding the medial flow passage. The body of the coupling has a second end portion that includes a first tube fitting communicating with the inner flow passage in the first end portion of the body, a second tube fitting communicating with the medial flow passage in the first end portion of the body and a third tube fitting communicating with the outer flow passage in the first end portion of the body.

These and other features of the coupling system of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the coupling system of the subject invention without undue experimentation, preferred embodiments thereof will be described in detail herein below with reference to certain figures, wherein.

DETAILED DESCRIPTION OF PREFERRED EMBODIMENTS

Figure 1:
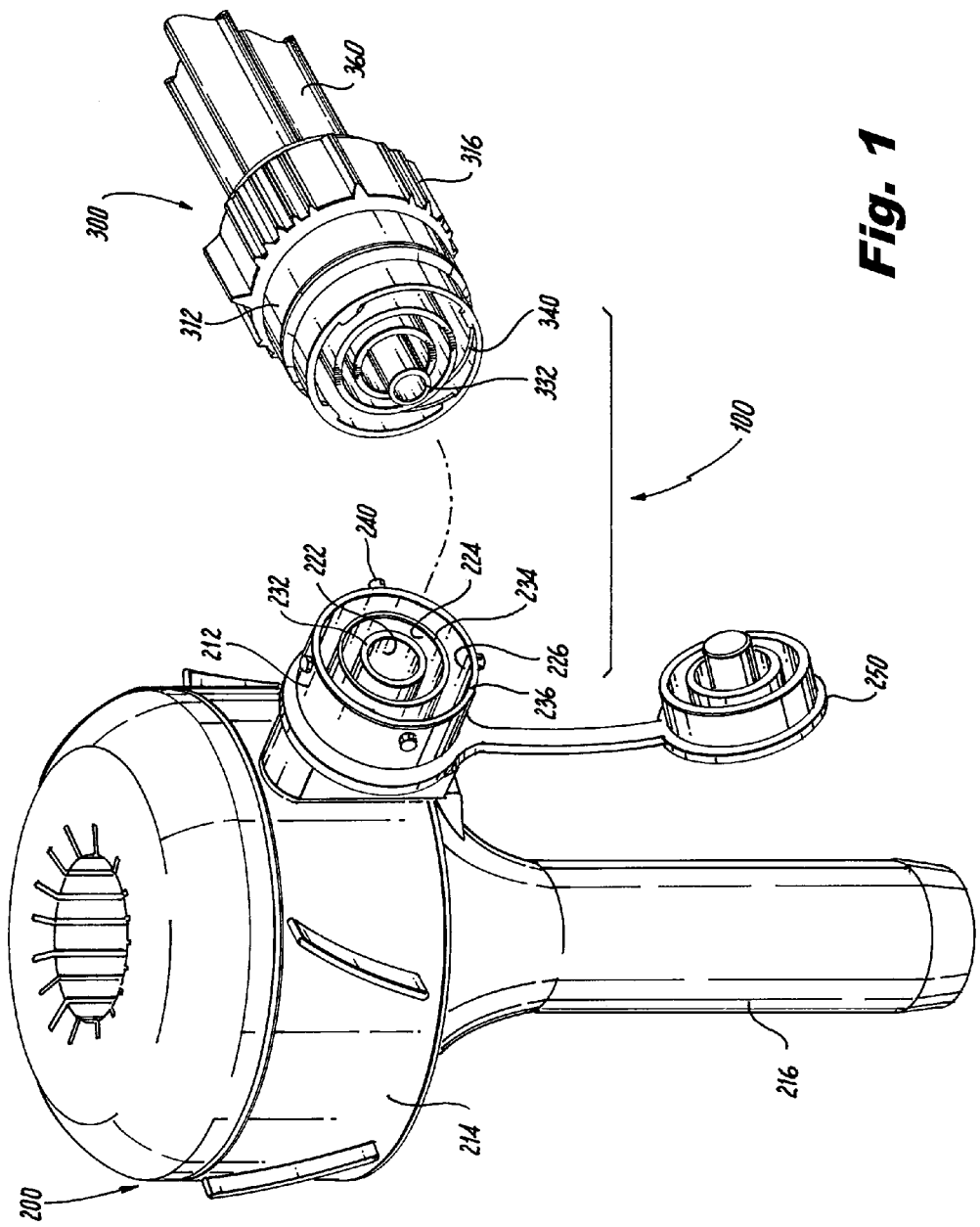
FIG. 1 is a perspective view of the coupling assembly of the subject invention, which is adapted and configured to connect a tube set to a trocar.

Referring now to the drawings wherein like reference numerals identify similar structural features and/or elements of the subject matter disclosed herein, there is illustrated in FIG. 1 a system for releasably coupling a tube set to a surgical device constructed in accordance with a preferred embodiment of the subject invention and designated generally by reference numeral 100.

Referring to FIG. 1, the coupling system 100 includes a surgical device 200 having a connector portion 212, and a tube set 300 including a coupling 312 adapted and configured to selectively connect with the connector 212 of the surgical device 200 through rotational engagement of the coupling 312 or a portion thereof with respect to the connector 212. In the embodiment of the invention illustrated in FIG. 1, the surgical device 200 is a multi-lumen trocar that includes a housing portion 214 supporting the connector 212 and a cannula portion 216 extending downwardly from the housing portion 214 and including coaxial inner and outer lumens (not shown), as disclosed for example in U.S. Pat. No. 7,854,724, which is incorporated herein by reference in its entirety.

With continuing reference to FIG. 1, the connector 212 is integrally formed with and extends radially outwardly from the housing portion 214 of surgical device (trocar) 200. The connector 212 is a generally cylindrical structure having a plurality of flow passages therein, which are defined by three concentric annular walls. More particularly, the connector 212 includes a central flow passage 222 defined by an inner annular wall 232, a medial flow passage 224 defined between a medial annular wall 234 and the inner annular wall 232, and an outer flow passage 226 defined between an outer annular wall 236 and the medial annular wall 234.

Each of the flow passages 222, 224 and 226 of connector 212 communicates with a separate fluid path formed within the housing 214 of trocar device 200. For example, one of the flow passage communicates with an abdominal pressure sensing/insufflation path, another with a pressurized gas path and another with a recirculation return path. These features of the trocar 200 are explained in more detail in U.S. Pat. No. 7,854,724, and shall not be discussed in detail herein.

The connector 212 also includes a plurality of circumferentially spaced apart camming lugs 240 for rotatably interacting with corresponding engagement structures associated with the coupling 312 of tube set 300, which will be described in further detail hereinbelow. Four camming lugs are shown as an exemplary embodiment. However, fewer lugs or more lugs can be used. The camming lugs 240 project radially outwardly from the exterior surface of the outer annular wall 236 of connector 212.

A rubber safety cap or stopper 250 is tethered to the connector 212 for closing off the three flow passage 222, 224 and 226 of the connector 212. The safety cap prevents contaminants from entering the flow passages of the trocar 200 when it is not in use. The tether prevents the cap 250 from becoming displaced from the trocar 200.

Figure 2:
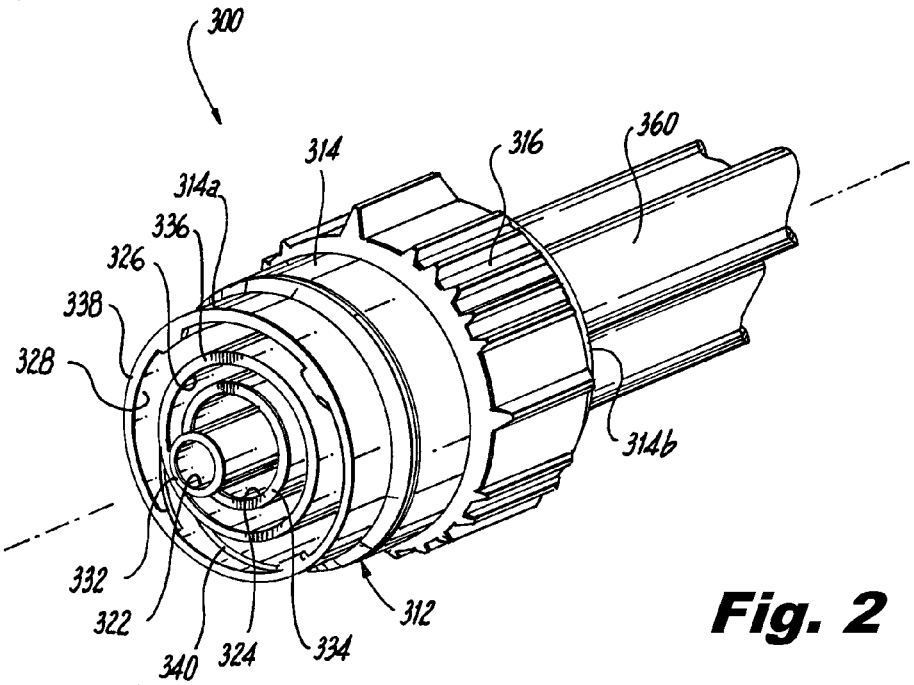
FIG. 2 is perspective view of the coupling of the subject invention, attached to the end of the tube set.

Referring now to FIG. 2, the coupling 312 of tube set 300 includes an elongated generally cylindrical body 314 having opposed distal and proximal end portions 314a and 314b. An annular gripping section 316 circumscribes the body 314 adjacent the proximal end portion 314b for facilitating the rotational engagement of the coupling 312 and the connector 212 during use, as will be described in more detail below.

The distal end portion 314a of coupling body 314 includes a plurality of flow passages channels and flow passage defined by a four concentric annular walls. More particularly, the distal end portion 314a of coupling body 314 includes a central flow passage 322 defined by an inner annular wall 332, a medial flow passage 324 defined between a medial annular wall 334 and the inner annular wall 332, and an outer flow passage 326 defined between an outer annular wall 336 and the medial annular wall 334. Additionally, the distal end portion 314a of coupling body 314 includes a surrounding annular engagement channel 328 defined between a surrounding annular wall 338 and the outer annular wall 336.

Figure 4:
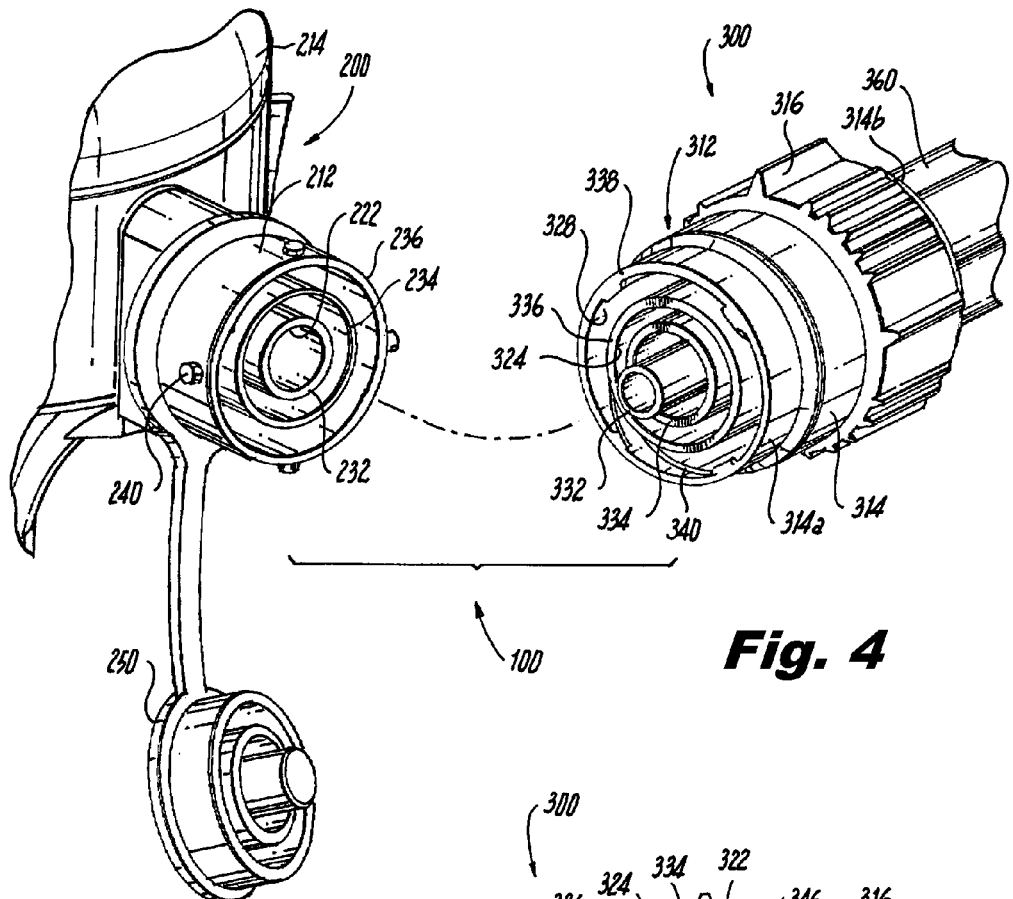
FIG. 4 is a localized view of the coupling assembly as shown in FIG. 1.

Referring now to FIG. 4, to enable the coupling 312 of tube set 300 to mate or otherwise engage with the connector 212 of trocar 200, the outer diameter of the inner annular wall 332 of coupling 312 is less than the inner diameter of the inner annular wall 232 of connector 212. Similarly, the outer diameter of the medial annular wall 334 of coupling 312 is less the inner diameter of the medial annular wall 234 of connector 212, and the outer diameter of the outer annular wall 336 of coupling 312 is less than the inner diameter of the outer annular wall 236 of connector 212. In addition, the inner diameter of the surrounding annular wall 338 of coupling 312 is greater than the outer diameter of the outer annular wall 236 of connector 212. The relative sizing of theses annular walls facilitates the complementary intimate engagement of the connector 212 and coupling 312.

Furthermore, the inner annular wall 332 of the inner flow passage 322 of coupling 312 extends forwardly from the distal end portion 314a of coupling 312 to act as a piloting feature with respect to the central flow passage 222 in connector 212 during the mating engagement of the connector 212 and coupling 312.

Figure 8:
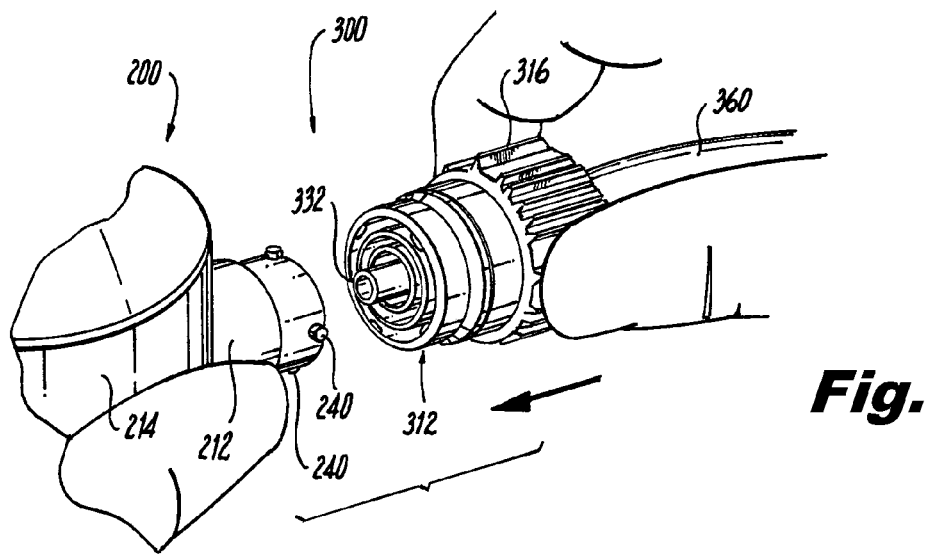
FIGS. 8 through 10 illustrate the steps for rotationally engaging the coupling with the connector on the trocar.
Figure 9:
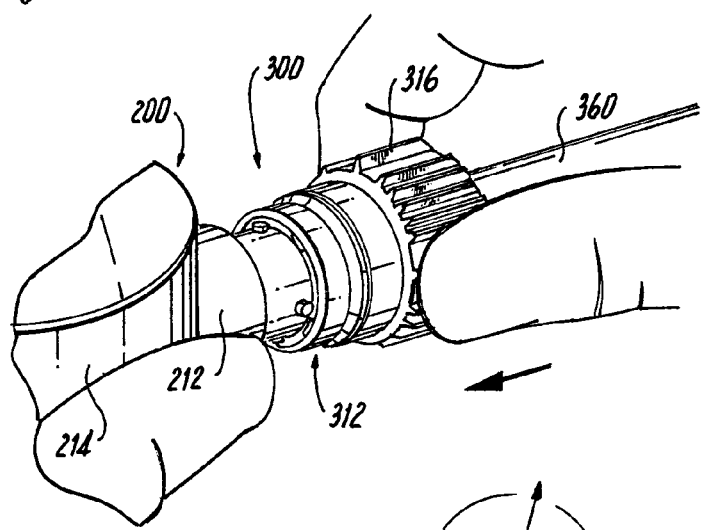
Figure 10:
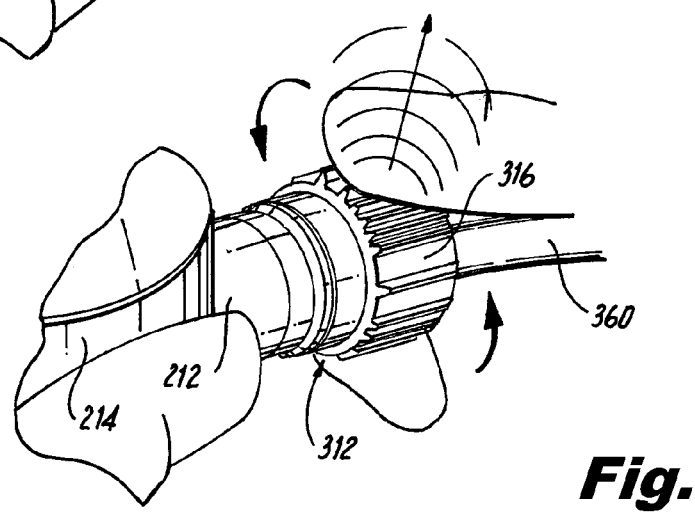

With continuing reference to FIG. 4, the interior surface of the surrounding wall 338 of coupling body 314 includes a plurality of spiraling camming ledges 340 that project radially inwardly from the wall 338. The spiraling cam ledges 340 are dimensioned and configured to interact with the camming lugs 240 that project radially outwardly from the exterior surface of the outer annular wall 236 of connector 212, when the coupling 312 is rotatably engaged with the connector 212, as illustrated in FIGS. 8 through 10.

Figure 3:
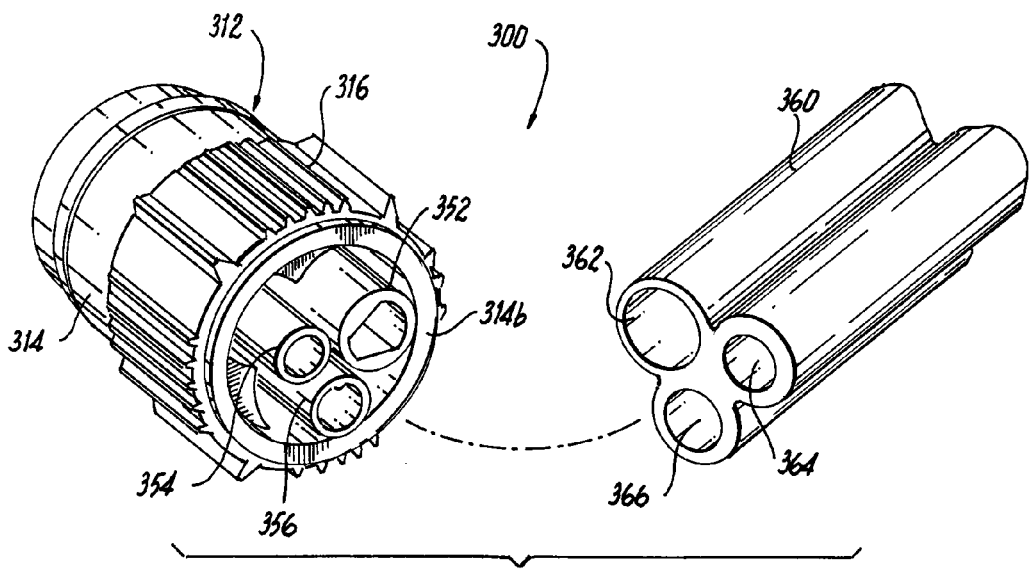
FIG. 3 is a perspective view of the coupling shown in FIG. 2, detached from the tube set.

Referring now to FIG. 3, the proximal end portion 314b of the coupling body 314 is operatively associated with a length of extruded tri-lumen flexible tubing 360. More particularly, the coupling body 314 includes a first, second and third parallel tube fittings 352, 354 and 356 for respectively mating or otherwise connecting with the first, second and third parallel lumens 362, 364 and 366 of the tri-lumen tubing 360. The connections between the tube fittings of the coupling body 314 and the lumens of the tubing 360 can be an interference fit or they can be fixedly attached by other means known in the medical device art.

Figure 5:
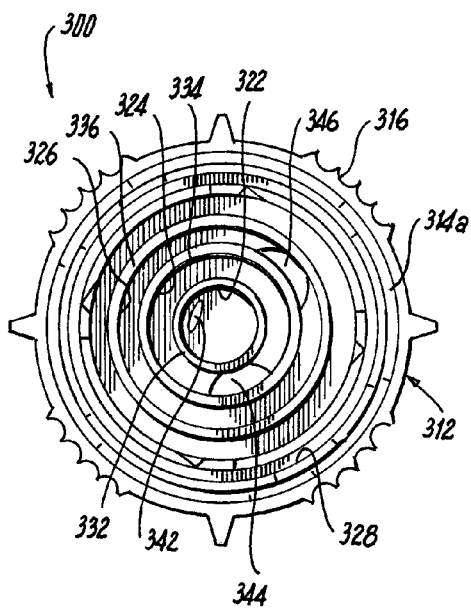
FIG. 5 is a front end view of the coupling assembly.
Figure 6:
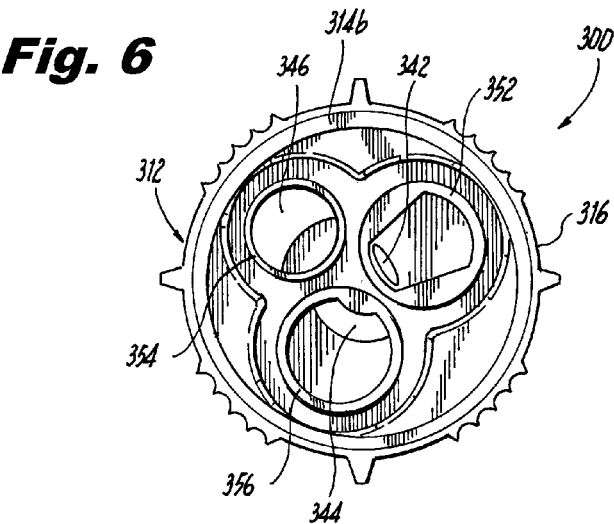
FIG. 6 is a rear end view of the coupling assembly.

As best seen in FIGS. 5 and 6, the tube fittings 352, 354 and 356 in the proximal end portion 314b of coupling body 314 are in direct fluid communication the flow passages 322, 324 and 326 in the distal end portion 314a of coupling body 314. More particularly, the first tube fitting 352 in is in direct fluid communication with the central flow passage 322 through a junction opening 342, the second tube fitting 354 is in direct fluid communication with the medial flow passage 324 through a junction opening 344, and the third fitting 356 is in direct fluid communication with outer flow passage 326 through a junction opening 346. Consequently, the lumens 362, 364 and 366 of tubing 360 are in fluid communication with flow passage 322, 324 and 326, respectively.

Figure 7:
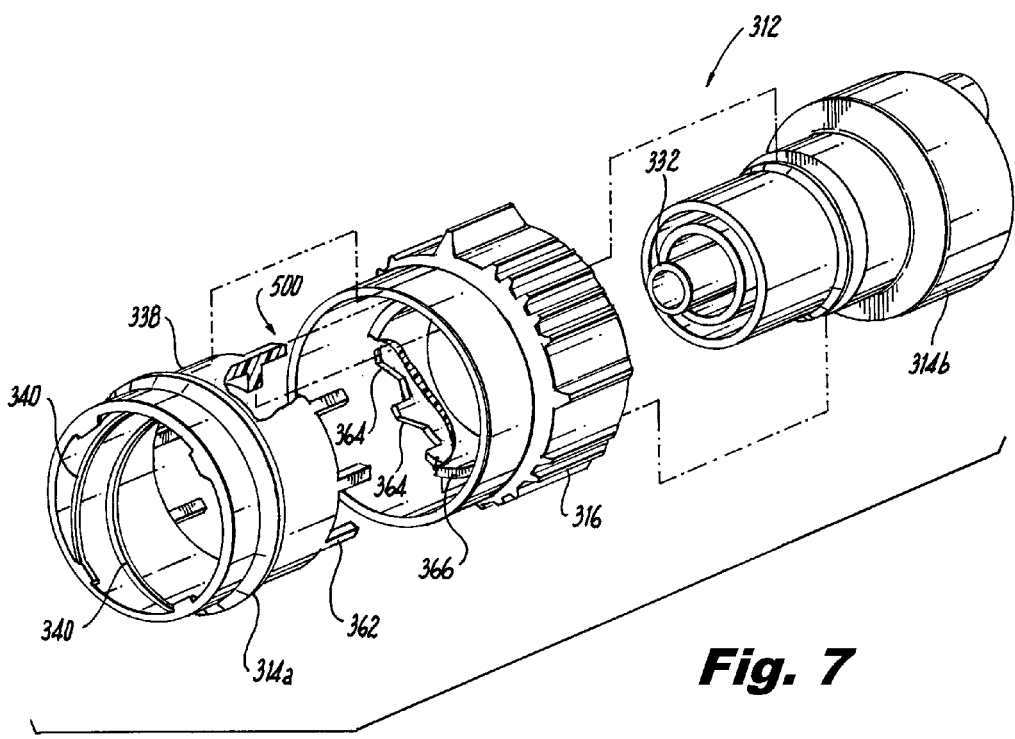
FIG. 7 is an exploded perspective view of the coupling assembly with parts separated for ease of illustration.

Referring now to FIG. 7, the coupling 312 includes a ratcheting clutch mechanism designated generally by reference numeral 500, which is configured to ensure that a predetermined amount of torque is applied during the rotational engagement of the coupling 312 of tube set 300 with the connector 212 of the trocar 200. The ratcheting clutch mechanism 500 includes the rotatable annular gripping section 316 and the surrounding wall portion 338 of the distal end portion 314a of coupling body 314.

Figure 11:
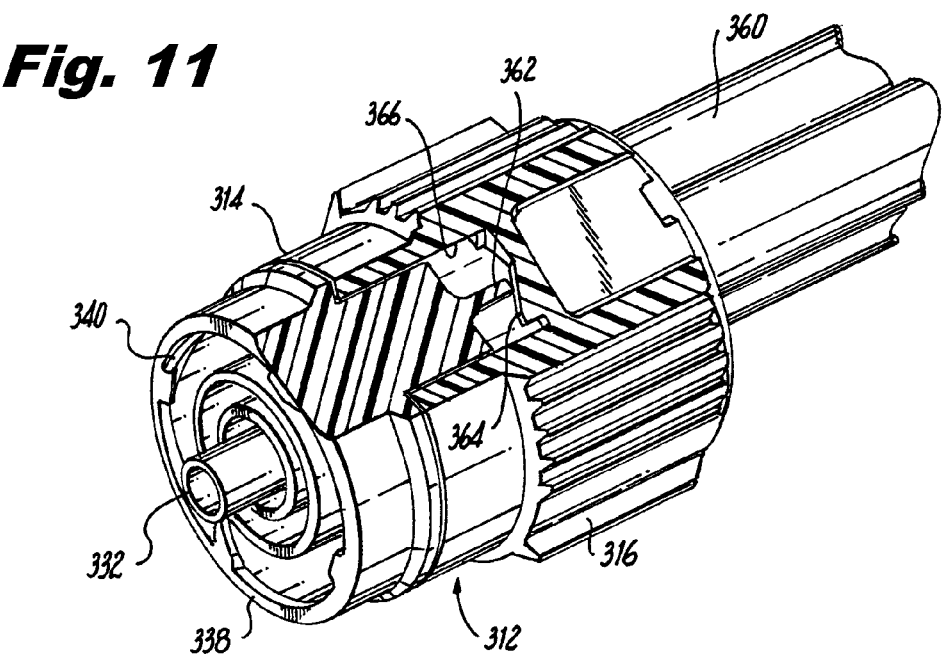
FIG. 11 is a perspective view of the coupling, with a portion thereof broken away to illustrate the ratcheting clutch mechanism that ensures a predetermined amount of torque is applied during the rotational engagement of the coupling with the connector of the trocar.
Figure 12:
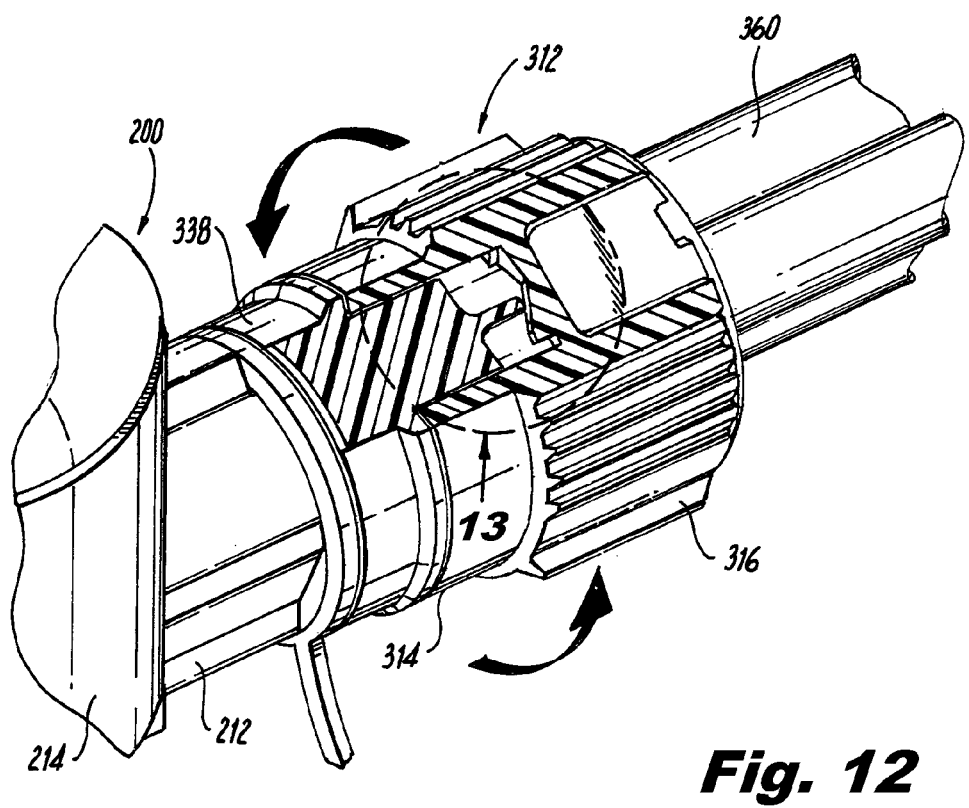
FIG. 12 is perspective view as in FIG. 11, illustrating the rotational engagement of the coupling and the connector of the trocar.

More particularly, a plurality of circumferentially spaced apart deflectable pawl arms 362 extend rearwardly from the surrounding annular wall 338 of coupling body 314. As illustrated in FIGS. 11 and 12, the pawl arms 362 are adapted and configured to interact with a plurality of circumferentially spaced apart ramped surfaces 364 that are formed within an interior annular channel 366 of the annular gripping section 316, when the annular gripping section 316 of coupling 312 is rotated relative to the coupling body 314.

Figure 13:
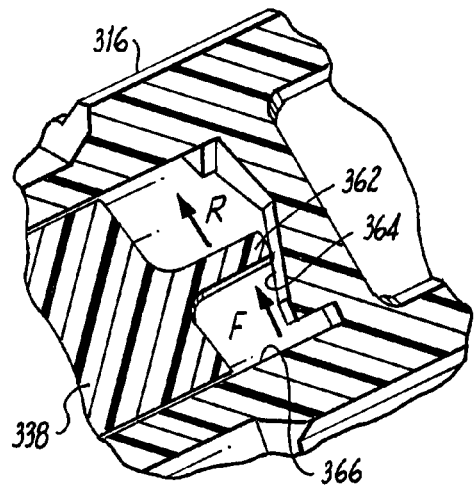
FIGS. 13-15 illustrate the interaction of the pawl and the rack of the ratcheting clutch mechanism.
Figure 14:
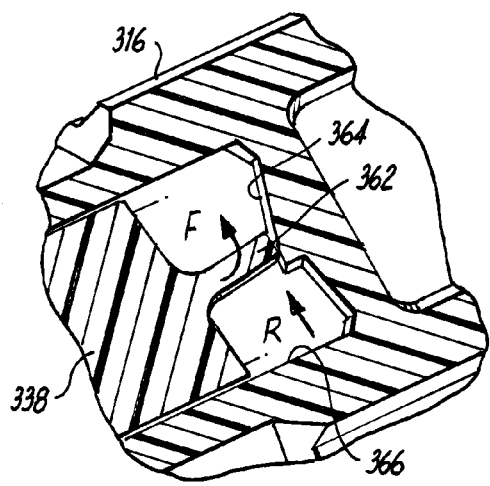
Figure 15:
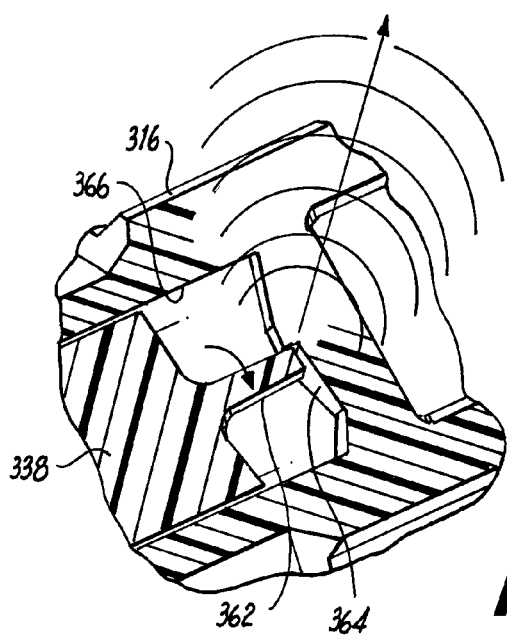

In use, when the annular gripping section 316 is rotated in a counter-clockwise direction (i.e., in the direction of indicator arrow "R" in FIG. 13), the ramped surfaces 364 cause the pawl arms 362 to deflect (i.e., in the direction of indicator arrow "F" in FIG. 14). When a ramped surface 364 travels beyond pawl arms 362, as seen in FIG. 15, the pawl arm 362 returns to its normal unflexed position. As such a time, the pawl arm 362 generates an audible clicking sound that will indicate to the user that the necessary amount of torque has been applied to the coupling. Once that has occurred, further rotation of the annular gripping section 316 of the coupling relative to the surrounding wall 328 of the coupling body 314 will not result in over-torqueing the connection.

Figure 16:
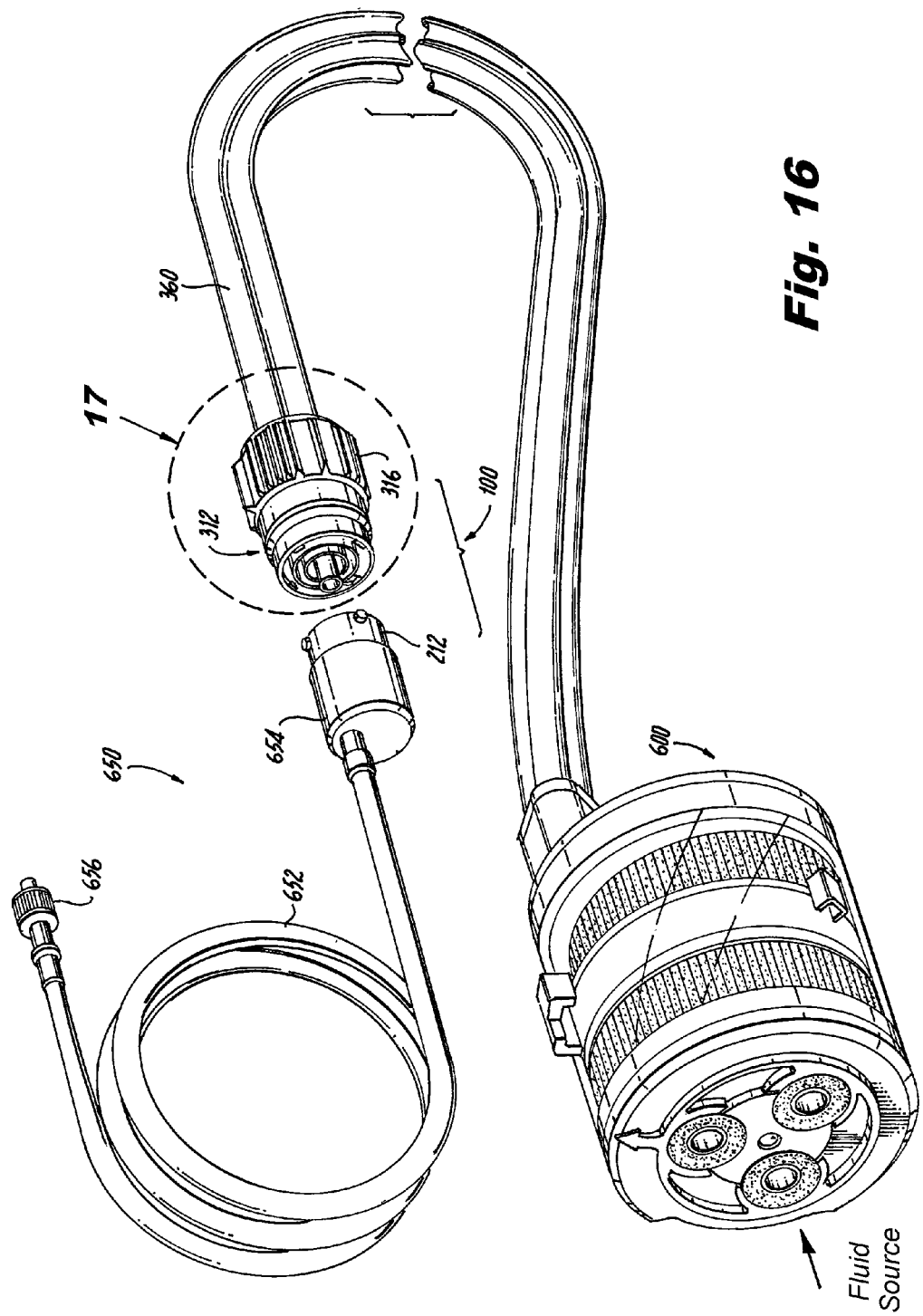
FIG. 16 is a perspective view of an embodiment of the coupling system of the subject invention, wherein the tube set is operatively connected to a filter assembly and the connector is associated with a secondary tube set.
Figure 17:
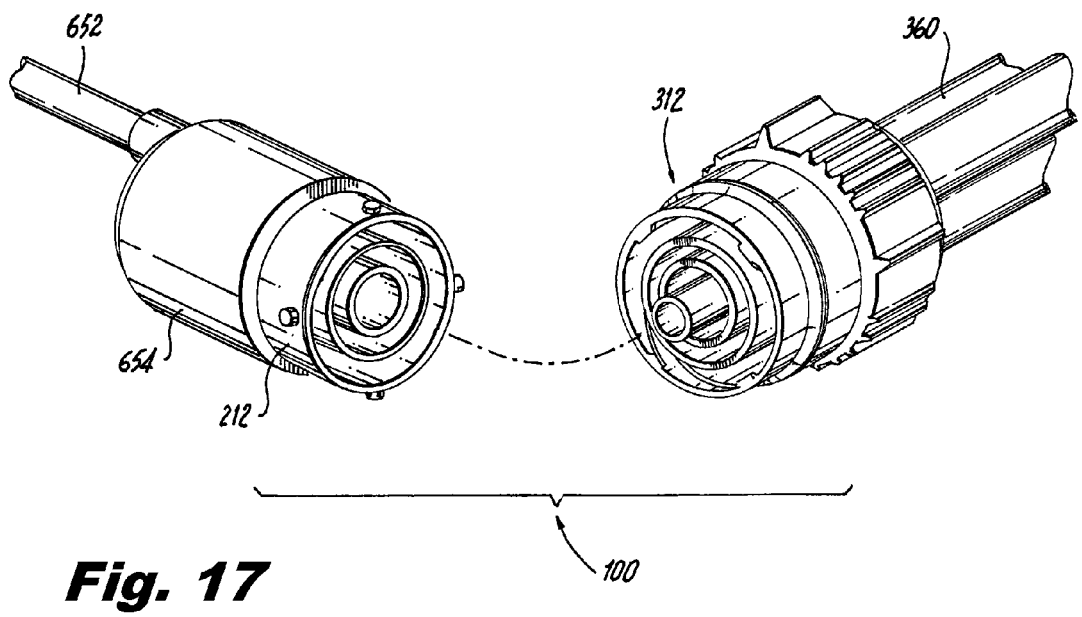
FIG. 17 is an enlarged localized view of the coupling system illustrated in FIG. 16.

Referring now to FIGS. 16 and 17, there is illustrated another embodiment of the coupling system 100 of the subject invention, wherein the coupling 312 is shown in conjunction with a tri-lumen tube set 360 and a disposable filter cartridge 600. The filter cartridge 600 is of the type disclosed in U.S. Pat. No. 7,976,598, for example. In this embodiment, the connector 212 is associated with a secondary tube set 650. The secondary tube set 650 includes a single lumen 652 having a housing 654 at one end and a leur fitting 656 at an opposite end for connecting with a single lumen trocar (not shown).

Figure 18:
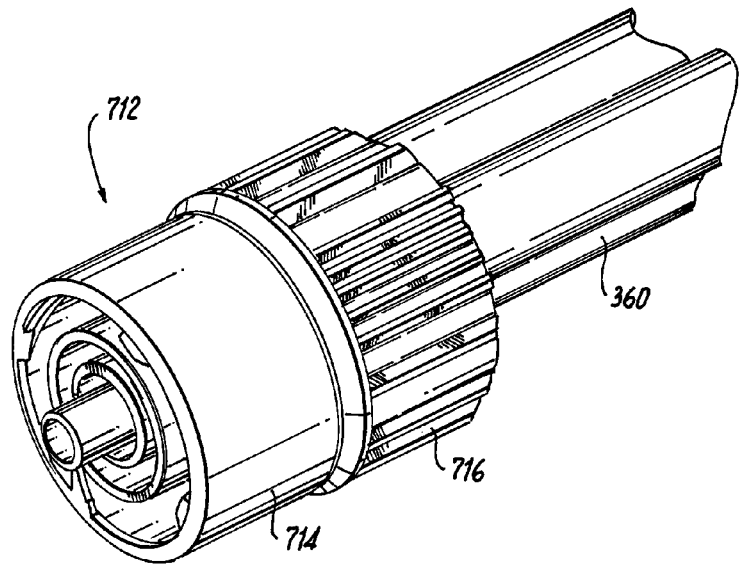
FIG. 18 is a perspective view of a coupling assembly constructed in accordance with another embodiment of the subject invention, which includes an integral body but does not include a ratcheting clutch mechanism.
Figure 19:
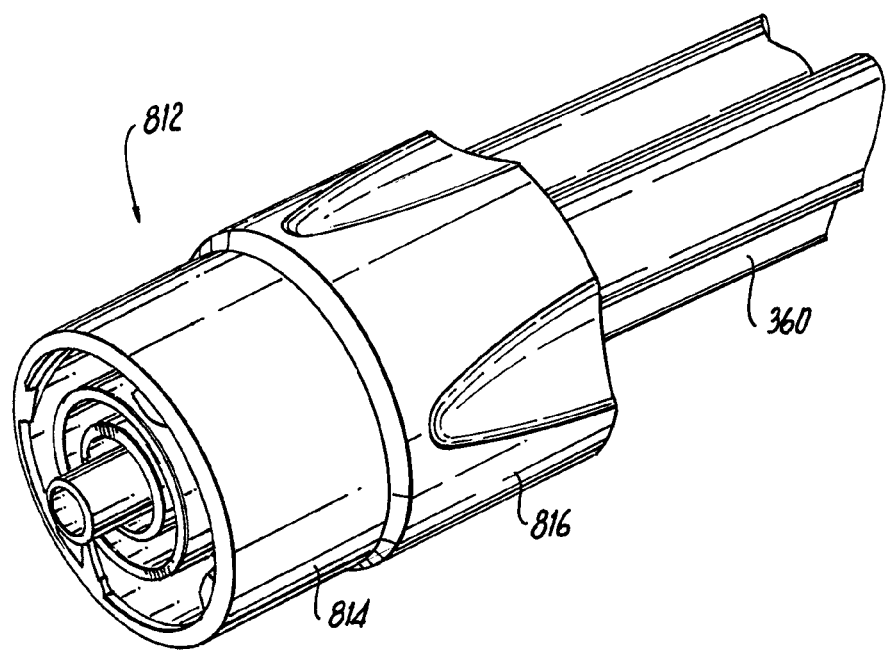
FIG. 19 is a perspective view of a coupling assembly constructed in accordance with another embodiment of the subject invention, which also does not include a ratcheting clutch mechanism.

Referring to FIG. 18, there is illustrated another embodiment of a coupling constructed in accordance with the subject invention, which his designated by reference numeral 712. Coupling 712 is substantially similar to coupling 312, except that the annular gripping section 716 does not rotate relative to the coupling body 714. Instead, the gripping section 716 has a fixed position relative to the coupling body 714. This embodiment also does not include a ratcheting clutch mechanism, as in the previous embodiment. A similar coupling 812 is illustrated in FIG. 19, which also includes an annular gripping section 816 that does not rotate relative to the coupling body 814.

While the subject invention has been shown and described with reference to preferred embodiments, those skilled in the art will readily appreciate that various changes and/or modifications may be made thereto without departing from the spirit and scope of the subject invention as defined by the appended claims. Moreover, those skilled in the art will readily appreciate that the coupling system of the subject invention can be used in multi-flow applications that are outside of the medical device field. For example, the coupling system can be used in multi-flow applications within the chemical processing, agricultural, automotive or aerospace industries. Those skilled in the art should also appreciate that the direction of fluid flow within each of the discrete fluid paths can vary depending upon the multi-flow application with which the coupling system is employed.

What is claimed is:

1. A coupling system for connecting a tube set to a trocar comprising:
   a) a multi-lumen trocar having a housing that defines a central axis and includes a connector, the connector extending radially outwardly from the central axis of the housing and having a plurality of coaxial flow passages defined therein by a plurality of concentric annular walls, wherein the connector has a longitudinal axis that extends perpendicular to the central axis of the housing of the trocar, and the coaxial flow passages of the connector are axially aligned with the longitudinal axis of the connector, wherein the plurality of coaxial flow passages of the connector includes a central flow passage defined by an inner annular wall, a medial flow passage defined between a medial annular wall and the inner annular wall, and an outer flow passage defined between an outer annular wall and the medial annular wall;
   b) a multi-lumen tube set including a plurality of tubes arranged in a parallel relationship; and
   c) a coupling including a generally cylindrical body having a first end portion adapted and configured to selectively mate with the coaxial flow passages of the connector of the trocar and a second end portion adapted and configured for attachment to the parallel tubes of the tube set, wherein the first end portion of the body of the coupling has a plurality of flow passages including an inner flow passage defined by an inner annular wall for establishing fluid communication with the central flow passage of the connector, a medial flow passage defined between a medial annular wall and the inner annular wall and surrounding the inner flow passage of the coupling for establishing fluid communication with the medial flow passage of the connector, and an outer flow passage defined between an outer annular wall and the medial annular wall and surrounding the medial flow passage of the coupling for establishing fluid communication with the outer flow passage of the connector.

2. The coupling system as recited in claim 1, wherein the second end portion of the body of the coupling includes a plurality of parallel tube fittings for mating with the tubes of the tube set.

3. The coupling system as recited in claim 1, wherein the second end portion of the body of the coupling includes a first tube fitting communicating with the inner flow passage in the first end portion of the body, a second tube fitting communicating with the medial flow passage in the first end portion of the body and a third tube fitting communicating with the outer flow passage in the first end portion of the body.

4. The coupling system as recited in claim 3, wherein the first end portion of the body of the coupling includes an annular engagement channel defined between an interior wall of the body of the coupling and the outer flow passage in the first end portion of the coupling, the annular engagement channel including radially inwardly projecting cam ledges for interacting with radially outwardly projecting cam lugs on aft the outer annular wall of the connector of the trocar, when the coupling is rotationally engaged with the connector of the trocar.

5. The coupling system as recited in claim 1, wherein an outer peripheral portion of the body of the coupling includes an annular gripping section to facilitate rotational engagement of the coupling with the connector of the trocar.

6. The coupling system as recited in claim 5, wherein the annular gripping section is formed integral with the body of the coupling.

7. The coupling system as recited in claim 5, wherein the annular gripping section includes an annular collar formed separate from and mounted to rotate relative to the body of the coupling.

8. The coupling system as recited in claim 7, wherein the annular gripping section includes at least part of a ratcheting clutch mechanism configured to ensure that a predetermined amount of torque is applied during rotational engagement of the coupling with the connector of the trocar.

9. The coupling system as recited in claim 8, wherein a first portion of the ratcheting clutch mechanism is associated with an inner peripheral surface of the annular collar and a second portion of the ratcheting clutch mechanism is associated an outer peripheral surface of the body of the coupling.

10. The coupling system as recited in claim 1, wherein the coupling is associated with one end of the tube set and a disposable filter cartridge is associated with an opposite end of the tube set.

11. The coupling system as recited in claim 1, wherein the multi-lumen trocar includes a cannula that extends from the housing and includes coaxial inner and outer lumens.

12. A coupling system for connecting a surgical device to a tube set comprising:
  a) a connector operatively associated with a housing of a surgical device, the connector having a plurality of coaxial flow passages defined therein by a plurality of concentric annular walls, wherein the connector has a longitudinal axis that extends perpendicular to a central axis of the housing of the surgical device, and the coaxial flow passages of the connector are axially aligned with the longitudinal axis of the connector, and wherein the plurality of coaxial flow passages includes a central flow passage defined by an inner annular wall, a medial flow passage defined between a medial annular wall and the inner annular wall, and an outer flow passage defined between an outer annular wall and the medial annular wall; and
  b) a coupling operatively associated with a tube set, the coupling including a generally cylindrical body having a first end portion that includes a plurality of concentric annular walls that are dimensioned for intimate engagement with the coaxial flow passages of the connector through rotational engagement of the coupling with respect to the connector, wherein the first end portion of the body of the coupling has a plurality of flow passages including an inner flow passage defined by an inner annular wall for establishing fluid communication with the central flow passage of the connector, a medial flow passage defined between a medial annular wall and the inner annular wall and surrounding the inner flow passage of the coupling for establishing fluid communication with the medial flow passage of the connector, and an outer flow passage defined between an outer annular wall and the medial annular wall and surrounding the medial flow passage of the coupling for establishing fluid communication with the outer flow passage of the connector.

13. The coupling system as recited in claim 12, wherein the body of the coupling has a second end portion that includes a first tube fitting communicating with the inner flow passage in the first end portion of the body, a second tube fitting communicating with the medial flow passage in the first end portion of the body and a third tube fitting communicating with the outer flow passage in the first end portion of the body.

14. The coupling system as recited in claim 12, wherein the inner annular wall of the inner flow passage of the coupling extends beyond the medial annular wall and the outer annular wall of the coupling to act as a piloting feature with respect to the central flow passage of the connector.

15. The coupling system as recited in claim 12, wherein the outer diameter of the inner annular wall of the coupling is less than the inner diameter of the inner annular wall of the connector, the outer diameter of the medial annular wall of the coupling is less than the inner diameter of the medical annular wall of the connector, and the outer diameter of the outer annular wall of the coupling is less than the inner diameter of the outer annular wall of the connector.

16. The coupling system as recited in claim 12, wherein the first end portion of the body of the coupling includes an annular engagement channel defined between an interior wall of the body of the coupling and the outer flow passage in the first end portion of the coupling, the annular engagement channel including radially inwardly projecting cam ledges for interacting with radially outwardly projecting cam lugs on the outer annular wall of the connector, when the coupling is rotationally engaged with the connector.

* * * * *